United States Patent [19]

Wang et al.

[11] Patent Number: 4,518,808

[45] Date of Patent: May 21, 1985

[54] PREPARATION OF 2,5-DICHLOROHYDROQUINONE

[75] Inventors: Richard H. S. Wang; Garry L. Myers, both of Kingsport, Tenn.

[73] Assignee: Eastman Kodak Company, Rochester, N.Y.

[21] Appl. No.: 537,227

[22] Filed: Sep. 29, 1983

[51] Int. Cl.$^3$ .............................................. C07C 37/62

[52] U.S. Cl. .................................... 568/765; 568/633; 568/634; 568/656; 568/726; 568/737; 568/779

[58] Field of Search ............... 568/779, 656, 726, 737, 568/765, 649

[56] References Cited

U.S. PATENT DOCUMENTS

| | | | |
|---|---|---|---|
| 2,151,137 | 3/1939 | Moness | 568/765 |
| 2,777,002 | 1/1957 | Sullivan | 568/779 |
| 2,902,518 | 9/1959 | Hurdis et al. | 568/726 X |

FOREIGN PATENT DOCUMENTS

| | | | |
|---|---|---|---|
| 839972 | 6/1960 | United Kingdom | 568/779 |

*Primary Examiner*—Bernard Helfin

*Attorney, Agent, or Firm*—Clyde L. Tootle; J. Frederick Thomsen

[57] ABSTRACT

Disclosed is a process for the preparation of certain dichloro-hydroxy and alkoxy aromatic compounds by reacting the corresponding unchlorinated compound with sulfuryl chloride in the presence of acetic acid, propionic acid or lower alkyl esters thereof.

1 Claim, No Drawings

PREPARATION OF 2,5-DICHLOROHYDROQUINONE

DESCRIPTION

This invention relates to a novel process for the preparation of dichloro-hydroxy and alkoxy aromatic compounds.

We have discovered that certain hydroxy and alkoxy aromatic compounds react with sulfuryl chloride in the presence of certain carboxylic acids or esters to produce a product which assays at least 80 percent dichloro compound. The prior art processes concerning the chlorination of hydroxy and alkoxy aromatic compounds, specifically the chlorination of hydroquinone, are not entirely suitable for the preparation of dichloro-hydroxy and alkoxy aromatic compounds, primarily because such processes give products which consist of mixtures of compounds which require uneconomical purification before they can be used further, for example, as monomers in various types of condensation polymers, as stabilizers in polymeric materials, and as intermediates for making other useful chemicals. Furthermore, we have found that only certain hydroxy and alkoxy aromatic compounds may be converted to the corresponding dichloro compounds in sufficient selectivity to avoid commercially impractical purification procedures.

Our novel process comprises the preparation of dichloro-hydroxy and alkoxy aromatic compounds selected from 2,5-dichlorohydroquinone, 3,6-dichlorocatechol, 4,6-dichlororesorcinol, 2,4-dichlorophenol, 4,6-dichloro-2-alkylphenol, 2,4-dichloro-5-alkylphenol, 2,6-dichloro-4-arylphenol, 2,4-dichloroalkoxybenzene, 2,5-dichloro-1,4-dialkoxybenzene, 2,4-dichloro-1-naphthol, 2,4-dichloro-1-alkoxynaphthalene and 2,2-bis(3-chloro-4-hydroxyphenyl)propane by reacting the corresponding unchlorinated compound with sulfuryl chloride in a mole ratio of about 2.0 to 2.2 moles of sulfuryl chloride per mole of unchlorinated compound in the presence of acetic acid, propionic acid or a lower alkyl (e.g. alkyl of up to about four carbon atoms) ester thereof, including mixtures of one or more acids and/or one or more esters such as methyl acetate, ethyl acetate, butyl acetate, and ethyl propionate. The carbon content of the alkyl and alkoxy substituents of certain of the reactants and products is not critical but normally will be up to about six carbon atoms with methyl and methoxy being the most common. The aryl substituent may be phenyl or alkyl-substituted phenyl.

The chlorination temperatures used may be varied widely, e.g. from about 15° to 110° C., depending on the particular compound being chlorinated. The chlorination promoting temperature preferably is in the range of about 30° to 80° C. except in the preparation of 2,5-dichlorohydroquinone and 2,4-dichloroalkoxybenzene which requires the use of higher temperatures, preferably in the range of about 60° to 100° C. Thus, under normal operating conditions, e.g. at atmospheric pressure, the preparation of 2,5-dichlorohydroquinone and 2,4-dichloroalkoxybenzene requires the use of a solvent which has a boiling point of about 60° C. or above.

Isolation of the product may be accomplished by adding the reaction mixture, preferably after removing a portion of the solvent by distillation, to a hydrocarbon solvent at elevated temperature. Upon cooling the product precipitates and can be separated by conventional solid-liquid separation techniques. Alternatively, the reaction mixture can be concentrated by removing all or a major portion of the reaction solvent and the chlorinated product can, without isolation, be reacted further, e.g. reacting the dichloro-hydroxy aromatic compounds with a dicarboxylic anhydride to form esters.

Our novel process is further illustrated by the following examples.

EXAMPLES 1-12

To a mixture of the hydroxy or alkoxy aromatic reactant (0.05 mol) and solvent (50 ml) is slowly added sulfuryl chloride (0.11 mol) with stirring over a period of 15-30 minutes, and the mixture is stirred an additional four hours. After removal of the solvent by distillation, hot toluene is added to dissolve the crude product and the mixture is filtered. The filtrate is cooled to precipitate the product which then is collected by filtration. In Example 9 the crude product is obtained simply by removing the solvent.

Table I sets forth the reactant, solvent and approximate temperature (exothermic reaction) employed and the product obtained in each example. The assay given for each product is the weight percent thereof which is the designated dichloro product as determined by gas chromatography, and the yield given is based on the theoretical amount of dichloro compound obtainable from the reactant.

TABLE I

| Example | Reactant | Temp., °C. | Solvent | Product | Assay/ Yield, % |
|---|---|---|---|---|---|
| 1 | Hydroquinone | 80 | HOAc[1] | 2,5-Dichlorohydroquinone | 94/61 |
| 2 | Catechol | 46 | MeOAc[2] | 3,6-Dichlorocatechol | 85/75 |
| 3 | Resorcinol | 42 | MeOAc | 4,6-Dichlororesorcinol | 99/75 |
| 4 | Phenol | 42 | MeOAc | 2,4-Dichlorophenol | 94/95 |
| 5 | o-Cresol | 46 | MeOAc | 2,4-Dichloro-6-methylphenol | 99/90 |
| 6 | m-Cresol | 45 | MeOAc | 2,4-Dichloro-5-methylphenol | 85/90 |
| 7 | 4-Phenylphenol | 41 | MeOAc | 2,6-Dichloro-4-phenylphenol | 97/80 |
| 8 | Anisole | 80 | HOAc | 2,4-Dichloroanisole | 94/80 |
| 9 | 1,4-Dimethoxybenzene | 45 | MeOAc | 2,5-Dichloro-1,4-dimethoxybenzene | 99/70 |
| 10 | 1-Naphthol | 40 | MeOAc | 2,4-Dichloro-1-naphthol | 95/85 |
| 11 | 1-Methoxynaphthalene | 44 | MeOAc | 2,4-Dichloro-1-methoxynaphthalene | 99/97 |
| 12 | Bisphenol A | 44 | MeOAc | 2,2-Bis(3-chloro-4-hydroxyphenyl)propane | 94/80 |

[1]Acetic acid
[2]Methyl acetate

The invention has been described in detail with particular reference to preferred embodiments thereof, but is will be understood that variations and modifications can be effected within the spirit and scope of the invention.

We claim:

1. Process for the preparation of 2,5-dichlorohydroquinone which comprises reacting hydroquinone with sulfuryl chloride in a mole ratio of about 2.0 to 2.2 mole of sulfuryl chloride per mole of unchlorinated compound at a temperature of about 60° to 100° C. in the presence of acetic acid, propionic acid or a lower alkyl ester thereof.

* * * * *